US00PP11057P

United States Patent [19]

Gillogly

[11] Patent Number: Plant 11,057

[45] Date of Patent: Sep. 14, 1999

[54] AVOCADO TREE NAMED 'DON GILLOGLY'

[76] Inventor: Don Gillogly, 2483 Doe Run Rd., Sequim, Wash. 98382

[21] Appl. No.: 08/934,533

[22] Filed: Sep. 22, 1997

[51] Int. Cl.[6] ..... A01H 5/00

[52] U.S. Cl. ..... Plt./200

[58] Field of Search ..... Plt./44, 200

[56] References Cited

U.S. PATENT DOCUMENTS

P.P. 4,957 11/1982 Bowker ..... Plt./44
P.P. 9,530 4/1996 Salas ..... Plt./44

*Primary Examiner*—Howard J. Locker
*Assistant Examiner*—Melissa L. Kimball

[57] ABSTRACT

A dwarf avocado tree producing two distinct crops per year of a green-skinned fruit with superior flavor and which said fruit turns black upon ripening.

3 Drawing Sheets

BACKGROUND OF THE INVENTION

This invention relates to a new and distinct variety of avocado tree named 'Don Gillogly'. The tree is notable for its vigor, hardiness, and small size and is unique because it blooms twice a year, in March and August, which means it produces two crops a year. The fruit is notable for its flavor and longevity.

The present variety of avocado tree was selected in 1991 from seedlings of the Hass cultivar, *Persea americana* ssp. *guatemalan.* The 'Hass' seed from which the aforementioned seedling selection grew, was planted several years prior to the seedling's discovery by the inventor on his property in the city of La Jolla, San Diego County, Calif., USA.

The new seedling was asexually reproduced in 1992 by T-budding, whip-grafting, saddle-grafting and saw kerf grafting at the inventor's home in California. Various rootstocks were used, including Lula, TopaTopa and Zutano. This resulted in several progeny trees which have continually displayed the growth and fruit characteristics typical of that found on the original tree. 'Don Gillogly' has grown and produced fruit in diverse climates such as La Jolla and Fremont, Calif.

BRIEF SUMMARY OF THE INVENTION

The primary distinguishing characteristics of the 'Don Gillogly' avocado tree are its superior fruit quality and its bearing habit. The skin of the fruit is smooth, and bright lustrous green, with yellow flecks on the slightly but smoothly pebbled areas. This bright shiny green skin turns black upon ripening which is a rarity with a green, smooth skinned avocado. The skin is thick and strong, with a secondary, buffering underskin which has the result of protecting it from bruising and, to a lesser degree, from frost damage. The flesh of the fruit bears a delicious rich flavor, without the sharp or bitter aftertaste sometimes found in the fruit of 'Hass'. The fruit does not darken upon slicing, ripens slowly, and thus has a long shelf life.

The avocado tree itself is unique in that it produces two crops a year. It is a small, vigorous plant which has survived frost unscathed in San Diego and the San Francisco Bay Area, when the 'Hass' trees nearby did not. It is very slow growing, makes an excellent container plant and has produced fruit indoors.

BOTANICAL DESCRIPTION OF THE PLANT

Figure 1:
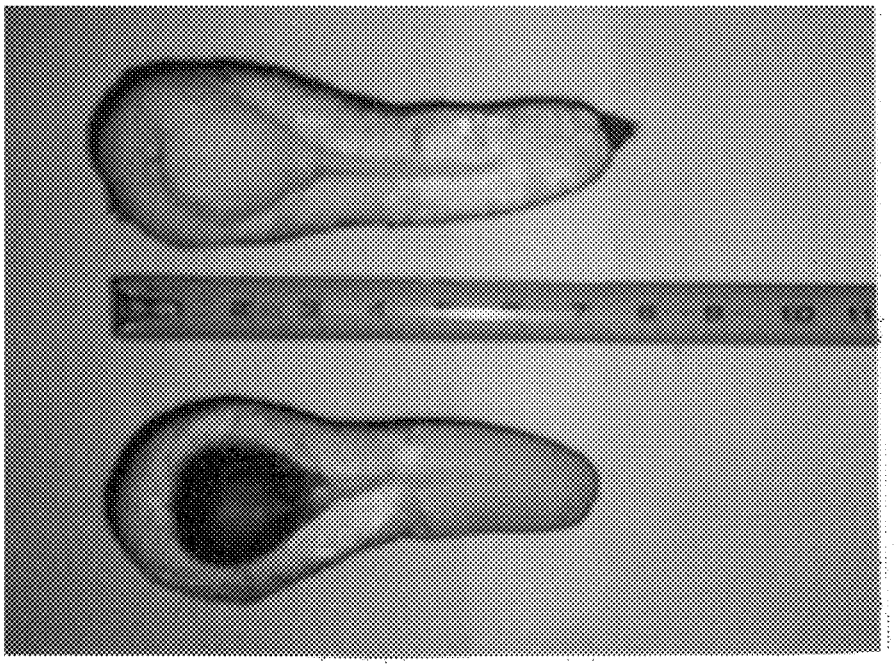
FIG. 1 illustrates the fruit of 'Don Gillogly' sectioned longitudinally.
Figure 2:
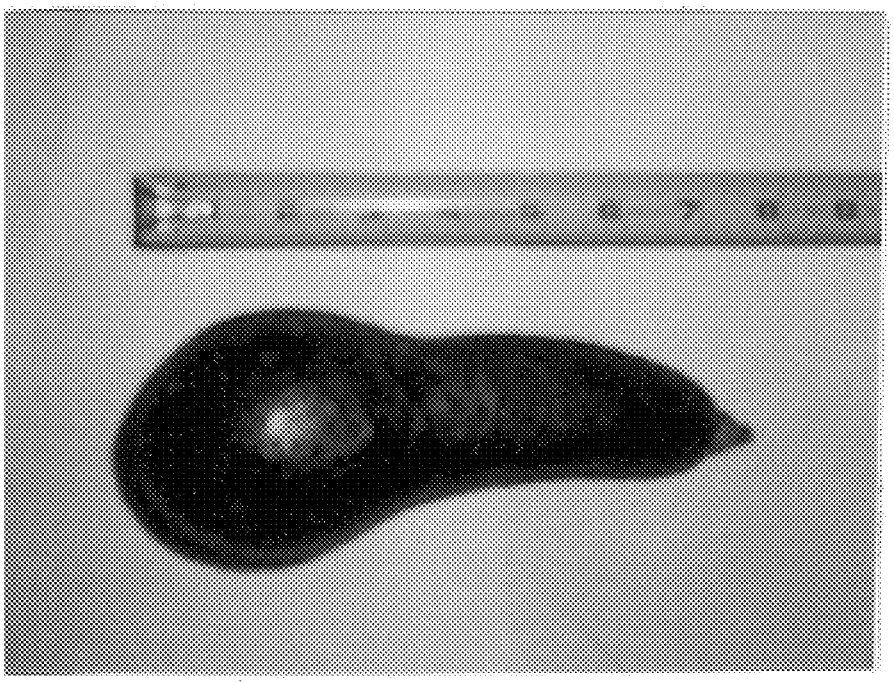
FIG. 2 shows the black skin of the ripened fruit.
Figure 3:
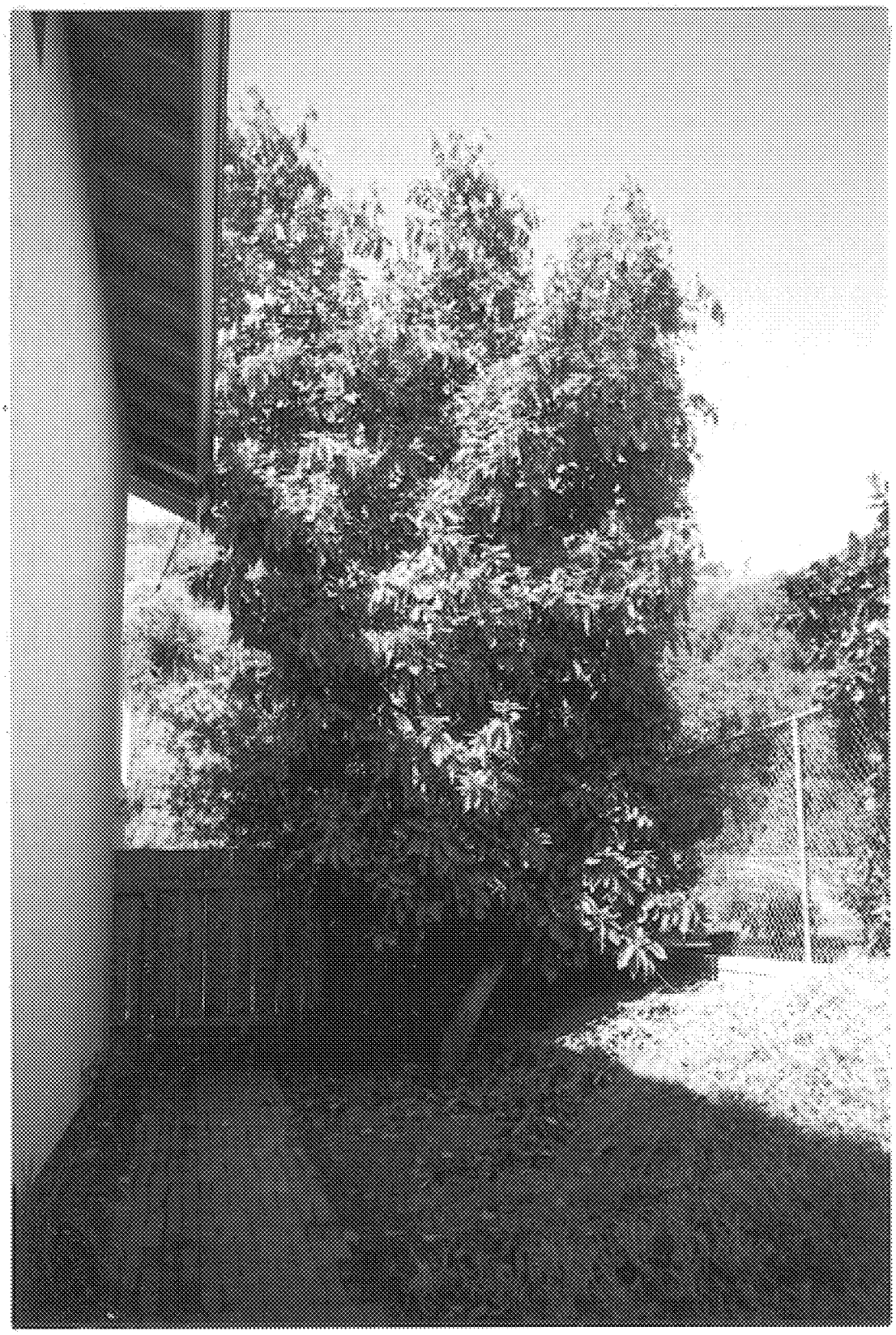
FIG. 3 shows the mature tree.
Figure 4:
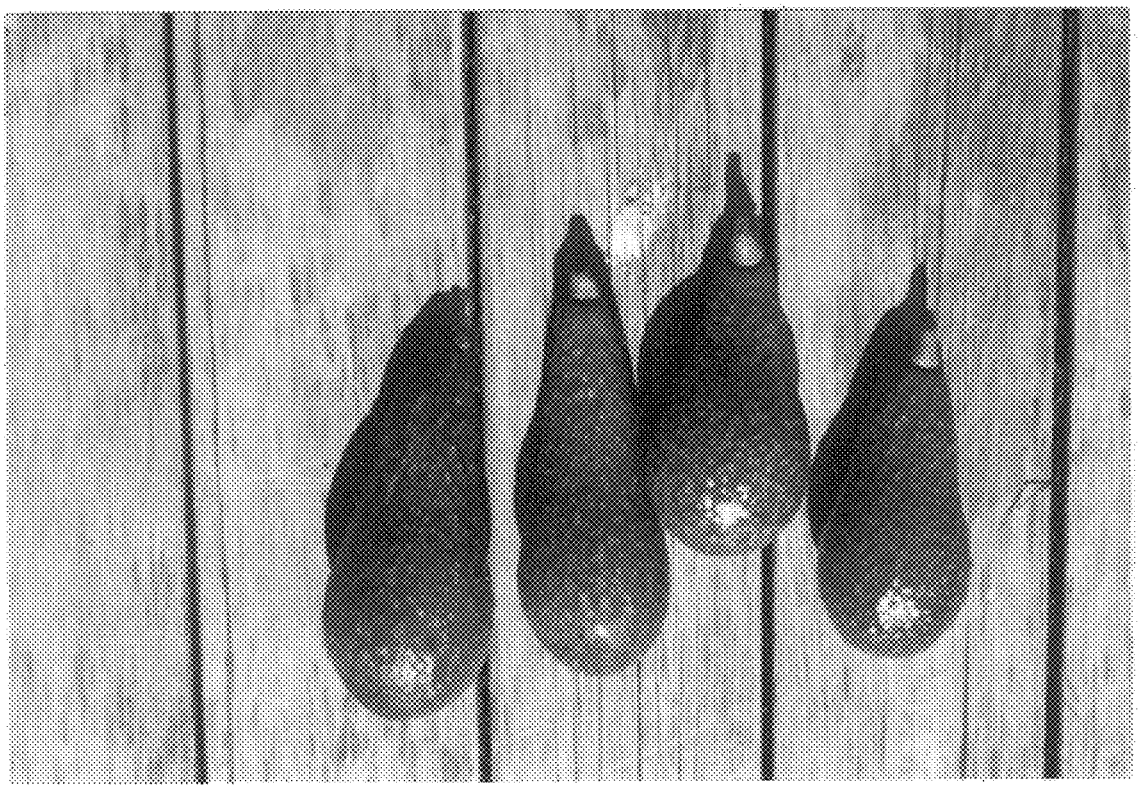
FIG. 4 shows unripened fruit.
Figure 5:
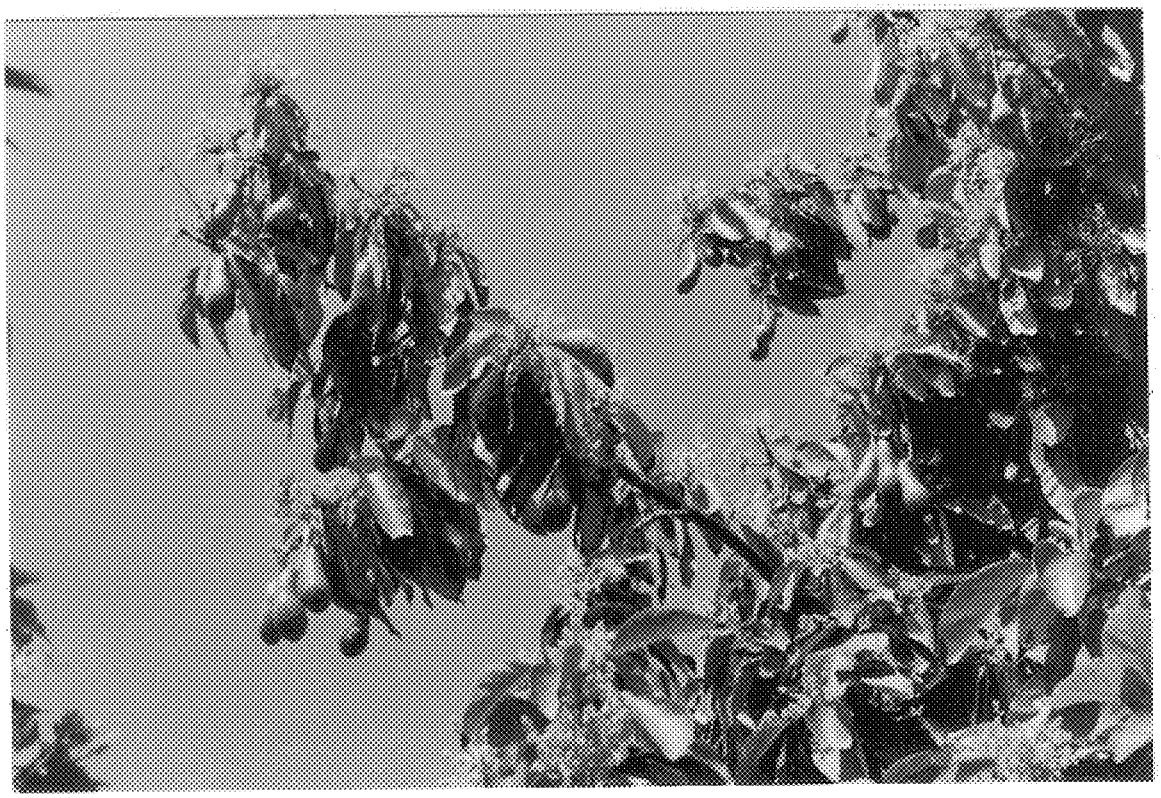
FIG. 5 shows a portion of the tree illustrating the inflorescence and various stages of fruit growth.

The following is a description of the new variety of avocado hereof named 'Don Gillogly', color terminology being in accord with colors taken from Munsell Corp., GretagMacBeth Division.

Tree:
- *Size.*—Dwarf. Very slow growth. About 14 feet in height at maturity.
- *Vigor.*—Quite vigorous.
- *Habit.*—Moderately upright.
- *Trunk.*—Medium to slender with tendency of two or more main branches.
- *Color of trunk.*—9.5 YR 3/7.5.
- *Branches.*—Upright, typical of species.
- *Yield.*—Heavy and seemingly constant as fruit at various stages of maturity are borne simultaneously.

Leaves:
- *Length.*—Variable up to 12 inches.
- *Width.*—Variable up to 4 inches.
- *Shape.*—Elliptic.
- *Color of mature leaves.*—6.5 GY 3.5/11.
- *Color of new leaf.*—4.5 GY 6/9.
- *Color of petioile.*—3.00 GY 6/12.
- *Aroma.*—No scent of licorice when crushed.

Flowers:
- *Size.*—Typical of species.
- *Season.*—Blooms in March and August.
- *Form.*—Multiple, profuse flower inflorescence.

Fruit, external characteristics:
- *Color.*—Background 9.36 GY 2.95/7.94.
- *Color.*—Flecks on Background 5.00 GY 9.5/10.
- *Shape.*—Predominately pear shaped.
- *Size.*—Diameter axial 3 inches. Maximum transverse diameter 7½ inches.
- *Weight.*—Average of 11–14 ounces.

*Skin.*—Thick, glass like smoothness, lustrous, with slightly raised pebbly flecks. Not rough or crumbly, but strong and protective.

Fruit, internal characteristics:

*Flesh color.*—5.00 Y 8/6.

*Texture.*—Buttery.

*Fibers.*—Few, fine.

*Ripening.*—March and second crop in August.

*Flavor.*—Rich, robust and flavorful; no harsh, bitter aftertaste.

*Oil content.*—Not tested but believed to be similar to 'Hass'.

*Eating quality.*—Exceptional.

Seed:

*Size.*—Medium, relative to size of fruit. Breadth 1½ inches. Length 2½ inches.

*Form.*—Ovoid.

*Surface.*—Smooth.

Having thus described and illustrated my new variety of avocado tree, what I claim as new and desire to be secured by Plant Letters Patent is:

1. A new and distinct variety of avocado tree as described and illustrated, characterized by the superior flavor of the fruit, the fact that it is a green-skinned fruit which turns black upon ripening, and that the tree is a dwarf, which produces two distinct crops per year.

* * * * *